(12) United States Patent
Kajita

(10) Patent No.: US 7,919,616 B2
(45) Date of Patent: Apr. 5, 2011

(54) CARBAPENEM COMPOUND

(75) Inventor: Satoshi Kajita, Takaoka (JP)

(73) Assignee: Nippon Soda Co., Ltd., Tokyo (JP)

( * ) Notice: Subject to any disclaimer, the term of this patent is extended or adjusted under 35 U.S.C. 154(b) by 483 days.

(21) Appl. No.: 12/084,351

(22) PCT Filed: Oct. 31, 2006

(86) PCT No.: PCT/JP2006/321722
§ 371 (c)(1),
(2), (4) Date: Apr. 29, 2008

(87) PCT Pub. No.: WO2007/052642
PCT Pub. Date: May 10, 2007

(65) Prior Publication Data
US 2009/0143574 A1    Jun. 4, 2009

(30) Foreign Application Priority Data
Nov. 2, 2005  (JP) .................... 2005-319343

(51) Int. Cl.
*C07F 9/572*     (2006.01)
(52) U.S. Cl. .................................... 540/302
(58) Field of Classification Search ............ 540/302
See application file for complete search history.

(56) References Cited

U.S. PATENT DOCUMENTS
4,382,949 A     5/1983  Afonso
2009/0118496 A1*  5/2009  Nishino et al. .......... 540/302

FOREIGN PATENT DOCUMENTS
JP   04-217985   8/1992
JP   04-330085   11/1992
JP   8-41063     2/1996
JP   2002-179679  6/2002

OTHER PUBLICATIONS

Search Report, European Patent Application No. 06822651.3, dated Jan. 7, 2009.
Japanese Patent Office, International Search Report (translated) and Written Opinion dated Dec. 12, 2006, from related International Patent Application No. PCT/JP2006/321722, filed on Nov. 2, 2006 (in Japanese).

* cited by examiner

*Primary Examiner* — Mark L Berch
(74) *Attorney, Agent, or Firm* — Kenyon & Kenyon LLP

(57) ABSTRACT

The present invention relates to a carbapenem compound represented by formula (Ia) shown below:

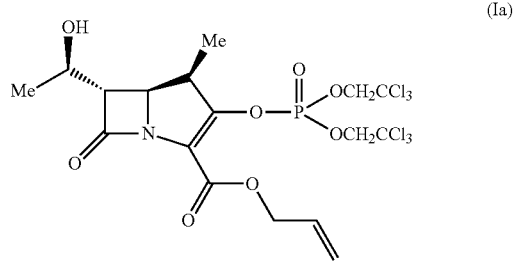

(Ia)

The carbapenem compound preferably has a crystalline form, and more preferably, the crystalline form has a powder X-ray diffraction pattern with peaks at 15.64, 9.93, 6.83, 6.52, 5.44, 5.01, 4.72, 4.50, 4.33, 4.24, 3.98, 3.85, 3.57, 3.41, 3.31, 3.10 2.76, and 2.67 as d-spacings (Å).

3 Claims, No Drawings

CARBAPENEM COMPOUND

This application is a national phase filing (35 U.S.C. §371) OF PCT/JP2006/321722, filed on Oct. 31, 2006, which claims priority under 35 U.S.C. §119 from Japanese application number JP 2005 319343, filed Nov. 2, 2005.

TECHNICAL FIELD

The present invention relates to a novel carbapenem compound which is a production intermediate of 2-(substituted mercapto)-1β-methyl-carbapenem antibiotics.

Priority is claimed on Japanese Patent Application No. 2005-319343, filed Nov. 2, 2005, the contents of which are incorporated herein by reference.

BACKGROUND ART

Since the discovery of thienamycin in 1976, research on the synthesis of carbapenem antibiotics has been vigorously carried out. Many carbapenem compounds which have excellent antibacterial activity, such as imipenum, have been discovered. However, many of these carbapenem compounds have the drawback that they are easily metabolized by renal dehydropeptidase-I (DHP-I)

Thus, research for improving stability against DHP-I has been vigorously carried and in 1984, the research group at Merck and Company Incorporated developed a 1β-methyl carbapenem compound that, while maintaining excellent antibacterial activity, was also chemically and physically stable as well as having excellent resistance against DHP-I.

Many research groups have since developed 2-(substituted mercapto)-1β-methyl-carbapenem antibiotics in which a substituted mercapto is introduced at the 2-position of the carbapenem skeleton and some of these are in practical use.

As such compounds, L-627 (biapenem) represented by formula shown below:

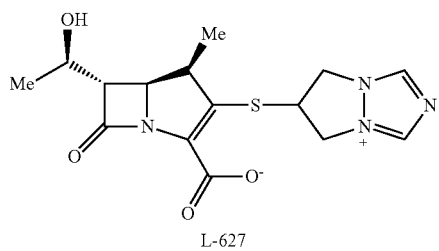

L-627

S4661 (doripenem) represented by formula shown below:

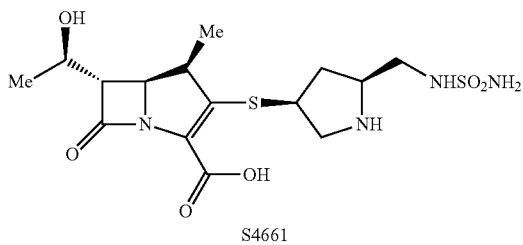

S4661 and SM7338 (meropenem) represented by formula shown below:

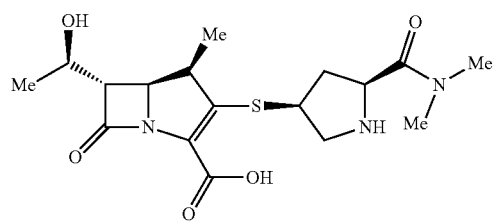

SM7338 have been developed, for example.

Conventionally, these 2-(substituted mercapto)-1β-methyl-carbapenem antibiotics are produced by the generally known method represented by reaction scheme shown below:

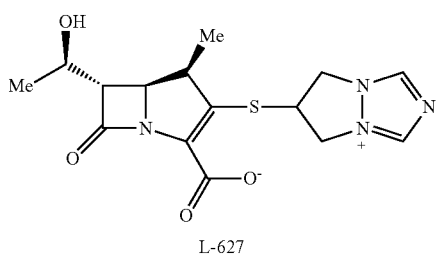

L-627

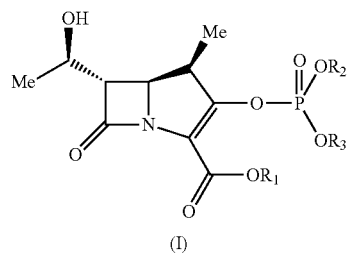

(I)

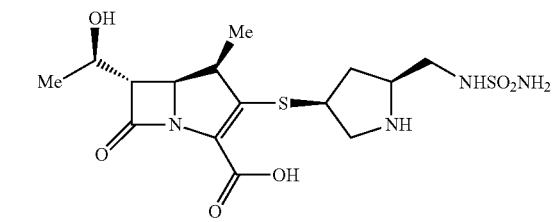

S4661

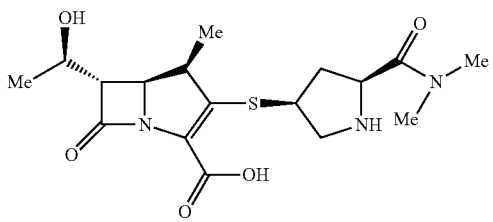

SM7338

In formula, $R_1$ represents a pharmaceutically-acceptable ester group or a carboxyl group protective group that can be easily removed; $R_2$ and $R_3$ each represents, independently, a phenyl group that may be substituted with a halogen atom, an alkyl group, a cyano group, a nitro group, or the like, a $C_1$ to $C_6$ alkyl group that may be substituted with a halogen atom, or the like; and X represents a halogen atom such as chlorine and bromine.

In other words, after deriving the phosphoric acid ester compound represented by formula (I) by reacting the compound represented by formula (II) with the compound represented by formula (III) in a suitable solvent such as acetonitrile in the presence of a base such as diisopropylethylamine, the final product is obtained by further reacting with mercaptans.

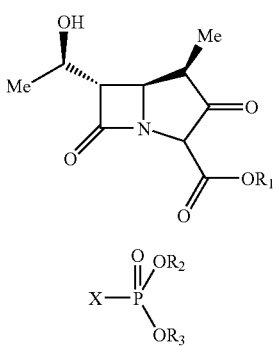

In above formulas, $R_1$ represents a pharmaceutically-acceptable ester group or a carboxyl group protective group that can be easily removed; $R_2$ and $R_3$ each represents, independently, a phenyl group that may be substituted with a halogen atom, an alkyl group, a cyano group, a nitro group, or the like, a $C_1$ to $C_6$ alkyl group that may be substituted with a halogen atom, or the like; and X represents a halogen atom such as chlorine and bromine.

In the above production method, the compound represented by formula (I) is an important production intermediate in the production of 2-(substituted mercapto)-1β-methyl-carbapenem antibiotics. It is preferable that this compound, particularly in situations where industrial-scale production is assumed, has high purity, is easily handable, and is in a crystalline form.

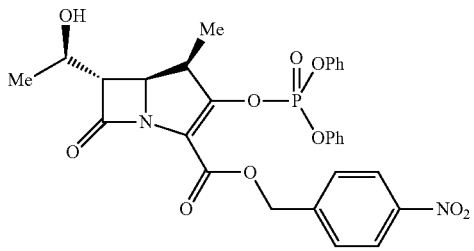

(Ib)

With respect to the compound represented by formula (I) shown above, Patent Document 1 discloses that the compound represented by formula (Ib) (hereinafter referred to as a "compound (Ib)") can be isolated in a crystalline form, for example. Also, this document discloses that the compound has excellent stability in the crystalline form and that it is useful as a bulk raw material. However, there are the problems that, by the reacted substrate, the reactivity of the diphenyl phosphoric acid part of the compound (Ib) is relatively poor and the ability to remove phosphoric acid is low.

Also, a p-nitrobenzyl group is used as the carboxyl group protective group in the compound (Ib). This group can be generally easily removed by a normal catalytic hydrogen reduction method using palladium carbon as the catalyst. However, the danger of fire from the filtration of palladium carbon and the use of hydrogen in an industrial process is high and thus the use of a p-nitrobenzyl group is unpreferable. Furthermore, production costs are relatively high when a p-nitrobenzyl group is used. A cheaper, more efficient, and stably-removable protective group is thus desired as the carboxyl group protective group instead of a p-nitrobenzyl group.

Related to the present invention, although Patent Document 2 discloses an example where $R_1$ is an alkyl group in formula (I) shown above, a specific synthesis example is hardly disclosed therein.

Patent Document 1: Japanese Unexamined Patent Application, First Publication No. Hei 4-330085

Patent Document 2: Japanese Unexamined Patent Application, First Publication No. Hei 4-217985

DISCLOSURE OF THE INVENTION

In consideration of the above circumstances of the prior art, the problem of the present invention is to provide a novel carbapenem compound which is a production intermediate of 2-(substituted mercapto)-1β-methyl-carbapenem antibiotics and which is easily handable, cheap, has high reactivity of the phosphoric acid ester part, and can easily remove the phosphoric acid ester part.

The present inventors have extensively studied about useful intermediates of 2-(substituted mercapto)-1β-methyl-carbapenem antibiotics in order to solve the above problem, and found that the compound represented by formula (Ia) shown below specifically crystallizes, that, by the reacted substrate, the reactivity of the phosphoric acid ester part of the compound represented by formula (Ia) is high and thus the phosphoric acid ester can be easily removed, and that, by the reacted substrate, the carboxyl group protective group of the compound represented by formula (Ia) can be easily removed, thus leading to completion of the present invention.

According to the present invention, a carbapenem compound represented by formula (Ia) shown below:

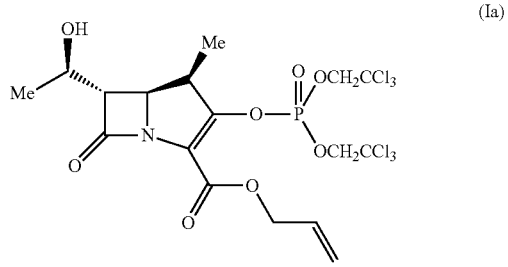

(Ia)

is provided.

It is preferable that the carbapenem compound of the present invention has a crystalline form and it is more preferable that the crystalline form has a powder X-ray diffraction pattern with peaks at 15.64, 9.93, 6.83, 6.52, 5.44, 5.01, 4.72, 4.50, 4.33, 4.24, 3.98, 3.85, 3.57, 3.41, 3.31, 3.10 2.76, and 2.67 as d-spacings (Å).

The compound of the present invention is similarly stable to the compound (Ib), which is a crystalline form bulk raw material that has heretofore been known as a production intermediate having a carbapenem skeleton.

Also, compared to the compound (Ib), the compound of the present invention, by the reacted substrate, has high reactivity of the phosphoric acid ester part and is a compound having an allyl group, which is comparatively cheap and easily removable, as a carboxyl group protective group.

The present invention is thus a further superior production intermediate of antibiotics having a carbapenem skeleton.

BEST MODE FOR CARRYING OUT THE INVENTION

The present invention will now be described in detail.

The present invention is the carbapenem compound represented by formula (Ia) shown above (compound name: allyl-(1R,5R,6S)-2-[bis(2,2,2-trichloroethyl)phosphoryloxy]-6-[(R)-1-hydroxyethyl]-1-methyl-carbapenem-3-carboxylate, hereinafter referred to as "compound of the present invention" or "compound (Ia)").

This compound is a novel substance.

The carbapenem compound of the present invention preferably has a crystalline form, and more preferably, the powder X-ray diffraction pattern has characteristic peaks at 15.64, 9.93, 6.83, 6.52, 5.44, 5.01, 4.72, 4.50, 4.33, 4.24, 3.98, 3.85, 3.57, 3.41, 3.31, 3.10 2.76, and 2.67 as d-spacings (Å).

The compound of the present invention can be prepared similarly to a method for preparing a well-known compound having a skeleton similar to that of the compound of the present invention.

For example, as disclosed in formula shown below, the compound of the present invention can be prepared by reacting the compound represented by formula (IIa) (compound name: allyl-(1R,5R,6S)-[(R)-1-hydroxyethyl]-2-oxo-carbapenem-3-carboxylate, hereinafter referred to as a "compound (IIa)") with a bis(2,2,2-trichloroethyl)phosphoryl halide represented by formula (IV) (hereinafter referred to as "bis(2,2,2-trichloroethyl)phosphoryl halide (IV)" in a suitable organic solvent in the presence of a base.

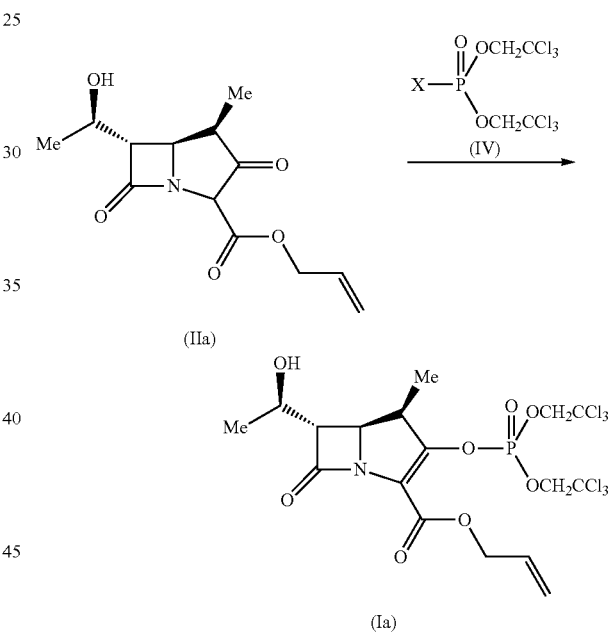

As the bis(2,2,2-trichloroethyl)phosphoryl halide (IV) used here, bis(2,2,2-trichloroethyl)phosphoryl chloride and bis(2,2,2-trichloroethyl)phosphoryl bromide can be given as examples.

The amount of the bis(2,2,2-trichloroethyl) phosphoryl halide (IV) used is normally 1 to 5 times the number of moles of the compound represented by formula (IIa).

As used bases, metal hydroxides such as sodium hydroxide and potassium hydroxide; metal alkoxides such as sodium methoxide, sodium ethoxide, magnesium ethoxide, and potassium t-butoxide; metal hydrides such as sodium hydride, potassium hydride, and calcium hydride; tertiary amines such as diisopropylethylamine and triethylamine; aromatic amines such as pyridine, 4-dimethylaminopyridine, picoline, and lutidine; and aliphatic cyclic amines such as 1,8-diazabicyclo[5.4.0]undec-7-ene (DBU) and 1,4-diazabicyclo[2.2.0]octane (Dabco) can be given as examples.

These bases may be used alone, or two or more thereof may be used in combination.

The amount of the base used is normally 1 to 5 times the number of moles of the bis(2,2,2-trichloroethyl)phosphoryl halide (IV).

As the used organic solvent, there are no particular limitations as long as the organic solvent is inactive to the reaction. Halogenated hydrocarbons such as methylene chloride and chloroform; amides such as N,N-dimethylformamide and N,N-dimethylacetamide; ether solvents such as tetrahydrofuran and 1,2-dimethoxyethane; esters such as ethyl acetate and propyl acetate; and nitriles such as acetonitrile can be given as examples.

The amount of the organic solvent used is normally 0.1 to 100 g based on 1 g of the compound represented by formula (IIa).

The reaction smoothly progresses in a temperature range from −50° C. to the boiling point of the solvent used, and preferably in a temperature range from −20° C. to +40° C.

The reaction time, which is dependent on the reaction scale, is usually from several minutes to several-tens hours.

After the reaction has been completed, normal aftertreatment operations and the like in organic synthetic chemistry are carried out. According to necessity, the target compound (Ia) can be isolated by carrying out separation and purification operations.

The structure of the target compound can be confirmed by a well-known analytical means such as IR spectroscopy, NMR spectroscopy, and mass spectroscopy.

In the present invention, it is preferred that the compound (Ia) is obtained in a crystalline form. In order to obtain the compound (Ia) in a crystalline form, a method shown by (i) or (ii) shown below, for example, can be used.

(i) A method in which the reaction mixture obtained by the carrying out of normal aftertreatment operations in organic synthetic chemistry on the above reaction solution is separated and purified by silica gel column chromatography, the fraction including the target product is concentrated, the concentrated product is dissolved in ethyl acetate, n-hexane is added thereto, and then cooled.

(ii) A method in which the organic layer is separated by adding water to the reaction solution, the separated organic layer is concentrated after drying the same over anhydrous magnesium sulfate, a mixed solvent of ethyl acetate and n-hexane is added thereto, and then the entirety is cooled.

The compound (IIa), which is a starting material, is a well-known compound and can be obtained by a well-known preparation method. For example, the compound (IIa) can be prepared by subjecting the compound represented by the below-mentioned formula (Va) (hereinafter referred to as a "compound (Va)") to ring closure in the presence of rhodium octanoate.

Also, in this situation, the target compound (Ia) can be obtained by, after carrying out the ring-closing reaction of the compound (Va), reacting the obtained reaction solution by adding a base and a bis(trichloroethyl)phosphoryl halide (IV).

When this method is used, crystals of the compound represented by formula (Ia) can be isolated by the method disclosed in (i) or (ii) shown above.

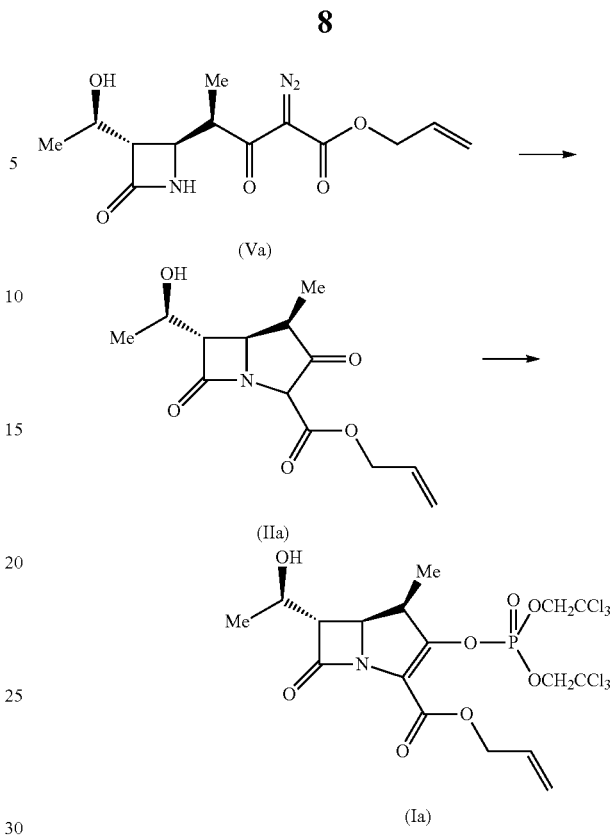

Although it is preferable to separate and use the compound of the present invention as crystals as disclosed above, the compound of the present invention can be used in a next step as is.

As is clear from the after-mentioned examples, the compound represented by formula (Ia) obtained in a crystalline form as disclosed above has a powder X-ray diffraction pattern with peaks at 15.64, 9.93, 6.83, 6.52, 5.44, 5.01, 4.72, 4.50, 4.33, 4.24, 3.98, 3.85, 3.57, 3.41, 3.31, 3.10 2.76, and 2.67 as d-spacings (Å) and is very stable in this crystalline form.

The compound of the present invention is similarly stable to a crystalline form bulk raw material which has heretofore been known as a production intermediate having a carbapenem skeleton (compound (Ib)). Compared to the compound (Ib), the compound of the present invention, by the reacted substrate, has high reactivity of the phosphoric acid ester part and is a compound having an allyl group, which is comparatively cheap and easily removable, as a carboxyl group protective group.

Compared to the compound (Ib), the present invention is thus a further superior production intermediate of antibiotics having a carbapenem skeleton.

EXAMPLES

The present invention will now be described in detail by way of examples.

Example 1

3.11 g of the compound (Va) was dissolved in 20 ml of ethyl acetate and 40.3 mg of rhodium octanoate dimer was added thereto at 40° C. This solution was heated to from 50° C. to 54° C. and after stirring for 40 minutes at this temperature, 4.07 g of bis(2,2,2-trichloroethyl)phosphoryl chloride and 13.7 mg of 4-(dimethylamino)pyridine were added under ice cooling. 1.45 g of diisopropylethylamine was added by dropping over 15 minutes at from −5° C. to 0° C. and after the completion of dropwise addition, the reaction solution was stirred for 30 minutes at from −5° C. to −3° C.

The reaction solution was washed twice with 10 ml of water and once with 10 ml of a 10% brine, and after drying over anhydrous magnesium sulfate, was concentrated under reduced pressure. The obtained brown oily residue was dissolved in 15 ml of ethyl acetate and 40 ml of n-hexane was added thereto by dropping at room temperature. The light brown powdery solid which precipitated after stirring the mixture for 1 hour at 0° C. was filtered and about 6.0 g of crude crystals was obtained by vacuum drying the filtered brown powdery solid.

After the obtained crude crystals were dissolved in 25 ml of ethyl acetate by heating, 25 ml of n-hexane was added thereto by dropping and white powdery crystals precipitated after stirring for 2 hours at room temperature. This white powder was filtered, and 2.81 g (45%) of needle crystals of the compound (Ia) was obtained by carrying out recrystallization again of the filtered white powder from 25 ml of ethyl acetate and 25 ml of n-hexane. The boiling point was 121 to 123° C.

$^1$H-NMR (CDCl$_3$, TMS) δ: 1.33 (3H, d), 1.34 (3H, d), 2.00 (1H, br), 3.35 (1H, dd), 3.45 (1H, m), 4.25 (2H, m), 4.6-4.9 (6H, m), 5.2-5.5 (2H, dd), 5.9-6.0 (1H, m)

$^{13}$C-NMR (CDCl$_3$, TMS) δ: 14.5, 21.8, 39.5, 54.2, 60.8, 65.5, 66.0, 77.6, 94.1, 118.9, 119.5, 131.0, 154.6, 158.8, 175.0

Measurement of Powder X-ray Diffraction of Compound (Ia)

Measurement of the powder X-ray diffraction of the compound (Ia) as obtained above was carried out. The measurement was carried out using an X-ray diffractometer (X'Pert PRO manufactured by Koninklijke Philips Electronics N.V.) The measurement results are shown in Table 1.

TABLE 1

Powder X-ray diffraction pattern

| Peak position | | Relative | Peak position | | Relative |
|---|---|---|---|---|---|
| 2θ (CuKα) | d-spacings [Å] | intensity [%] | 2θ (CuKα) | d-spacings [Å] | intensity [%] |
| 5.65 | 15.64 | 77.2 | 20.95 | 4.24 | 40.3 |
| 8.90 | 9.93 | 100.0 | 22.35 | 3.98 | 53.4 |
| 12.96 | 6.83 | 9.6 | 23.08 | 3.85 | 15.0 |
| 13.58 | 6.52 | 43.5 | 24.88 | 3.57 | 73.4 |
| 16.28 | 5.44 | 19.9 | 26.09 | 3.41 | 17.5 |
| 17.68 | 5.01 | 10.0 | 26.91 | 3.31 | 20.2 |
| 18.80 | 4.72 | 85.5 | 28.79 | 3.10 | 10.9 |
| 19.74 | 4.50 | 39.4 | 32.40 | 2.76 | 12.6 |
| 20.50 | 4.33 | 15.1 | 33.51 | 2.67 | 11.0 |

Stability Test of Compound (Ia) in Crystalline State

About 2 g of the compound (Ia) in a crystalline form which was obtained in the same way as Example 1 was placed in sample bottles, and the sample bottles were stored at room temperature (about 20° C.) and in a room maintained at a temperature of about 40° C. Taking the original purity as 100%, after every several number of days, the purity of the compound (Ia) was measured using high-performance liquid chromatography (HPLC). The HPLC measurement conditions are shown below. Also, the measurement results are shown in Table 2

Measurement Conditions

Solvent delivery system: LC-10A (manufactured by Shimadzu Corporation)
UV, VIS detector: SPD-10A (manufactured by Shimadzu Corporation)
Detection wavelength: 215 nm
Column heater: Sugai U-620 (used at 40° C., Sugai Chemical Industry Co., Ltd.)
Column: Inertsil® ODS-2 (4.6 mm diameter×250 mm length, GL Sciences, Inc.)

TABLE 2

| Temperature | Initial purity | 6 days | 17 days | 21 days | 31 days |
|---|---|---|---|---|---|
| 20° C. | 100% | 100% | 100% | 100% | 100% |
| 40° C. | 100% | 100% | 100% | 100% | 100% |

As shown in Table 2, from measuring the purity at 20° C. and 40° C. after 6 days, after 17 days, after 21 days, and after 31 days, the compound (Ia) in the crystalline form was very stable without a decrease in purity.

REFERENCE EXAMPLE

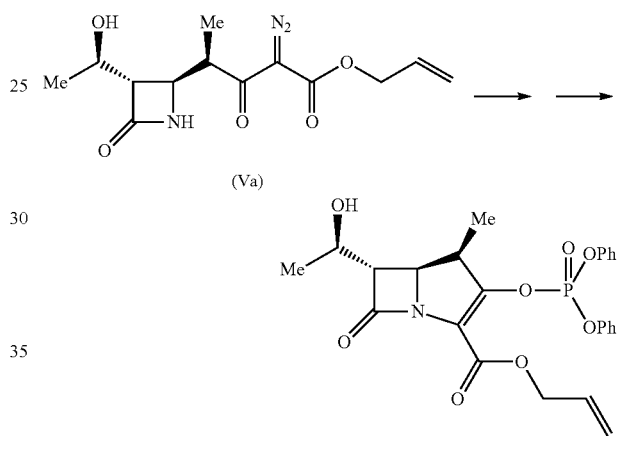

3.12 g of the compound (Va) was dissolved in 20 ml of ethyl acetate and 40.3 mg of rhodium octanoate dimer was added thereto at room temperature. This solution was heated to from 50° C. to 53° C. and after stirring for 45 minutes at this temperature, 3.00 g of diphenylphosphoryl chloride and 13.5 mg of N,N-(dimethyl)aminopyridine were added at −3° C. 1.43 g of diisopropylethylamine was added thereto by dropping over 5 minutes at from −3° C. to −2° C. After the reaction solution was stirred for 30 minutes at from −5° C. to −3° C., the reaction solution was washed twice with 10 ml of water and once with 10 ml of a 10% brine solution, and after drying over anhydrous magnesium sulfate, was concentrated under reduced pressure. The obtained brown oily residue was dissolved in 10 ml of ethyl acetate and 15 ml of n-hexane was added thereto by dropping at room temperature. Although the mixture was stirred for 3 hours at from −5° C. to 0° C., crystals of the compound (Ic) were not obtained.

INDUSTRIAL APPLICABILITY

As disclosed above, according to the present invention, a novel carbapenem compound which is a production intermediate of 2-(substituted mercapto)-1β-methyl-carbapenem antibiotics and which is easily handable, cheap, has high reactivity of the phosphoric acid ester part, and can easily remove the phosphoric acid ester part can be provided.

The invention claimed is:
1. A carbapenem compound represented by formula (Ia) shown below:
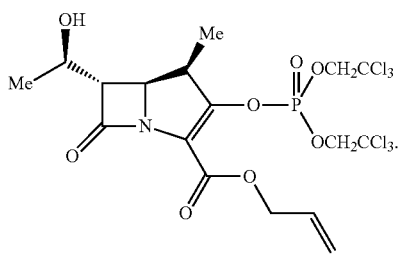
(Ia)
2. The carbapenem compound according to claim 1, wherein the carbapenem compound has a crystalline form.
3. The carbapenem compound according to claim 2, wherein the crystalline form has a CuKα X-ray diffraction pattern with peaks at 15.64, 9.93, 6.83, 6.52, 5.44, 5.01, 4.72, 4.50, 4.33, 4.24, 3.98, 3.85, 3.57, 3.41, 3.31, 3.10 2.76, and 2.67 as d-spacings (Å).
* * * * *